United States Patent [19]

Ricci et al.

[11] Patent Number: 5,395,992
[45] Date of Patent: Mar. 7, 1995

[54] SYNTHESIS OF DIOLS, FOR USE AS INTERMEDIATES FOR POLYMERIC MATERIALS, BY STARTING FROM TERMINAL DIOLEFINS

[75] Inventors: Marco Ricci, Novara; Francesco Gementi, Galliate; Francesco Panella, Pertengo; Cecilia Querci, Novara; Raffaele Ungarelli, Trecate, all of Italy

[73] Assignee: Enichem S.p.A., Milan, Italy

[21] Appl. No.: 14,528

[22] Filed: Feb. 8, 1993

[51] Int. Cl.$^6$ ............................................. C07C 27/00
[52] U.S. Cl. ...................................... 568/865; 549/531
[58] Field of Search ......................... 568/865; 549/531

[56] References Cited

U.S. PATENT DOCUMENTS 3,975,449  8/1976  Suzuki ................................. 568/865
4,731,482  3/1988  Venturello .......................... 549/531

FOREIGN PATENT DOCUMENTS 633326   12/1961  Canada ................................ 549/531
0493778   7/1992  European Pat. Off. .
1319093   1/1963  France .
1508939   1/1968  France .

*Primary Examiner*—Johann Richter
*Assistant Examiner*—Rebecca Cook
*Attorney, Agent, or Firm*—Oblon, Spivak, McClelland, Maier & Neustadt

[57] ABSTRACT

Disclosed is the synthesis of terminal diols, which are organic intermediates used in order to produce polymeric materials, by starting from terminal diolefins, which synthesis is based on the oxidation of diolefins to yield diepoxides, in a double-phase aqueous-organic system with hydrogen peroxide and in the presence of catalysts soluble in the organic phase, followed by a reaction of reduction of the resulting diepoxides.

6 Claims, No Drawings

SYNTHESIS OF DIOLS, FOR USE AS INTERMEDIATES FOR POLYMERIC MATERIALS, BY STARTING FROM TERMINAL DIOLEFINS

The present invention relates to the synthesis of terminal diols, by starting from terminal diolefins, which synthesis based on the oxidation of said diolefins in order to yield diepoxides in a double-phase, aqueous-organic system with hydrogen peroxide and in the presence of catalysts soluble in the organic phase, followed by a reaction of reduction of the resulting diepoxides.

The $\alpha$, omega-diols of general formula (I):

$$OH-(CH_2)_n-OH \qquad (I)$$

are compounds which are widely used in the sector of polymeric materials and, in particular, as monomers for polyesters and polyurethanes.

They are prepared through several routes which however display a validity which is often limited to just one of the compounds represented by formula (I).

So, a large number of processes exist for preparing ethylene glycol (in which n=2) or 1,4-butanediol (in which n=4), as described in Ullmann's Encyclopedia of Industrial Chemistry, Fifth Edition, Vol. A 10, pages 104–107 and Vol. A 4, pages 458–459.

The terms of the series in which n is higher than 4 are prepared, on the contrary, by means of the catalytic hydrogenation of the corresponding dicarboxy acids or their esters according to the following reaction:

$$\text{ROOC}-(CH_2)_{n-2}-\text{COOR} + 4H_2 \xrightarrow{\text{Catalyst}} OH-(CH_2)_n-OH + 2ROH$$

in which R=H or alkyl.

However, the hydrogenation cited above requires high pressures (150–450 atm) and equally high temperatures (150°–250° C.).

Furthermore, many dicarboxy acids are not easily available, or are only available in limited amounts.

Owing to these reasons, it would be desirable to have available a synthesis of $\alpha$, omega-diols of formula (I), which is suitable for a large number of terms of the series, and, simultaneously, cheap.

Recently, following the industrial developement of metatesis reactions, large amounts of alpha,omega-dienes of formula (II):

$$CH_2=CH-(CH_2)_{n-4}-CH=CH_2 \qquad (II)$$

have become available, which the present Applicant has found to constitute a considerably interesting starting material for the synthesis of $\alpha$, omega-diols of formula (I), without any of the drawbacks which affect the prior art.

Therefore, the subject-matter of the present invention is the synthesis of terminal diols of formula (I), in which $n \geq 8$, by starting from terminal diolefins having the formula (II), which synthesis is based on the following reactions carried out sequentially, with or without separation of the diepoxide (III) reported hereinunder:

(a) epoxidation of both double bonds of the formula (II);

(b) double, regioselective hydrogenation of the diepoxide (III) obtained in that way.

The reaction scheme is as follows:

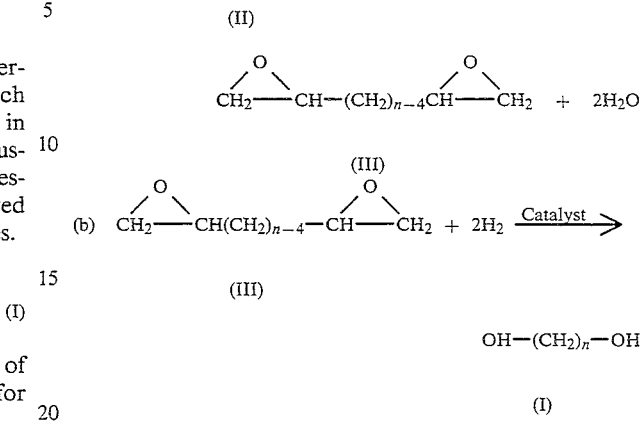

More particularly, diepoxides of formula (III) are prepared by oxidizing the diolefins (II) in the presence of hydrogen peroxide in a double-phase aqueous-organic system and in the presence of catalysts soluble in the organic phase, which are constituted by tetraalkylammonium phosphotungstates, according to as taught by italian patent application IT No. 24 154 A/82 to the same Applicant's name.

The reaction of bisepoxidation is carried out at a temperature comprised within the range of from 40° to 90° C. and using from 1.8 to 4 mols of hydrogen peroxide per each diolefin mol, and is complete within several hours.

As substrates, either straight or branched diolefins can be used, which contain not less than 8 carbon atoms, and may also be substituted with groups which are inert under the reaction conditions, such as ether, carbonate, halogen, nitro, carbonyl, carboxy, ester groups, and so forth.

Examples of such olefins are 1,7-octadiene, 1,9-decadiene, 1,13-tetradecadiene and 1,21-docosadiene.

The following reaction of hydrogenation of diepoxides (III) is carried out in a suitable solvent, under a moderate hydrogen pressure and in the presence of a heterogeneous catalyst constituted by Raney nickel.

As solvents, alcohols, such as ethanol, propanols, butanols; or hydrocarbon solvents, such as hexane, heptane, cyclohexane, methylcyclohexane; and so forth, may be used.

The concentration of diepoxide in the solvent is not critical for the purposes of process operations: in general, the process is carried out at concentrations comprised within the range of from 2 to 50%, preferably of from 5 to 10%, but higher or lower values are possible as well, although not always are they feasible.

The process is carried out at a temperature comprised within the range of from 20° to 150° C., preferably of from 20° to 120° C.

As regards hydrogen pressure, the process can be carried out at values comprised within the range of from 1 to 100 atm; however, due to obvious reasons, the process is preferably carried out under moderate pressure conditions, i.e., under a pressure generally comprised within the range of from 2 to 10 atm.

The used catalyst is, as already mentioned, Raney nickel, which is used in amounts of from 5 to 40% by weight relatively to the diepoxide and preferably of from 10 to 30%.

The level of activity of Raney nickel does not seem to be critical for the purposes of process operations: the best results were however obtained with the activity grade W2.

The reaction time depends on such operating conditions as temperature, hydrogen pressure, substrate concentration and catalyst amount, but, in general, is comprised within the range of from 0.5 to 8 hours.

In the following, some examples are reported in order to illustrate the present invention without limiting it.

EXAMPLE 1

Preparation of 1,2,9,10-diepoxydecane 71.1 g of 1,9-decadiene (0.515 mol), 4.28 g (1.55 mmol) of [dioctadecyl (75%)+dihexadecyl (25%)] dimethylammonium tetra(diperoxotungsto)phosphate [prepared as disclosed in italian patent application IT No. 22 555 A/85 (U.S. Pat. No. 4,731,482) to the same Applicant's name, in which the catalyst in question is indicated as $(C_{37}H_{78}N)_3PW_4O_{24}$], 34 ml of water and 100 ml of 1,2-dicloroethane were charged to a 4-necked flask of 0.5 l of capacity, equipped with mechanical stirrer, thermometer and reflux condenser.

The resulting mixture was heated, with strong stirring, up to 50° C. and, at that temperature, 108 g (1.05 mol) of hydrogen peroxide at 33% was dropwise added during a 6-hour time, with stirring being then continued for a further hour.

At the end the mixture was cooled, to it methylene chloride was added, and the phases were separated.

The organic phase was first rapidly distilled in order to remove the catalyst from it, then was rectified, with 47.0 g (0.276 mol) of 1,2,9,10-diepoxydecane, with a yield of 54%; 1.96 g of unreacted 1,9-decadiene (3%); and 23.0 g of 1,2-epoxy-9-decene (29%) being obtained.

EXAMPLE 2

Peparation of 1,10- decanodiol 10.0 g (57.9 mmol) of 1,2,9,10-diepoxydecane at 98.5%, 180 ml of ethanol and 2 g of Raney nickel with activity grade W2 were charged to an autoclave of stainless steel of 0.5 litre of capacity equipped with thermocouple and mechanical stirrer.

The resulting mixture was heated, with stirring, to 100° C., and then, at that temperature, hydrogen was fed under a pressure of 5 atm; the system was kept at these temperature and pressure values for 4 hours.

At the end, the reaction mixture was allowed to cool, hydrogen was vented off, the autoclave was purged with nitrogen, was emptied and Raney nickel was filtered off from the reaction mixture.

The gaschromatographic analysis of the filtrate, using 1,5-pentanediol as the internal standard, showed the presence of 5.71 g (32.8 mmol) of 1,10-decanediol (with a yield of 57%); 1.36 g (7.8 mmol) of 1,9-decanediol (13%); and 1.01 g (6.4 mmol) of 1-decanol (11%).

EXAMPLE 3

The conditions of Example 2 were repeated, with 250 ml of ethanol being used; therefore, the process was carried out under higher dilution conditions.

5.22 g (30.0 mmol) of 1,10-decanediol (with a yield of 52%); 1.23 g (7.1 mmol) of 1,9-decanediol (12%); and 1.23 g (7.7 mmol) of 1-decanol (13%) were obtained.

EXAMPLE 4

The conditions of Example 2 were repeated, by now operating under a pressure of 10 atm.

5.63 g (32.3 mmol) of 1,10-decanediol (with a yield of 56%); 1.74 g (10.0 mmol) of 1,9-decanediol (17%) and 0.96 g (6.1 mmol) of 1-decanol (10%) were obtained.

EXAMPLE 5

The conditions of Example 2 were repeated, with ethanol being replaced by tert-butanol.

3.87 g (22.2 mmol) of 1,10-decanediol (with a yield of 38%); 1.15 g (6.6 mmol) of 1,9-decanediol (11%) and 1.08 g (6.9 mmol) of 1-decanol (12%) were obtained. $(C_{37}H_{78}N)_3PW_4O_{24}$], 34 ml of water and 100 ml of 1, 2-dicloroethane

EXAMPLE 6

The conditions of Example 2 were repeated, with ethanol being replaced by cyclohexane.

3.67 g (21.1 mmol) of 1,10-decanediol (with a yield of 36%); 1.48 g (8.5 mmol) of 1,9-decanediol (15%); and 1.06 g (6.7 mmol) of 1-decanol (12%) were obtained.

We claim:

1. A process for preparing a $\alpha, \omega$-diol of formula (I):

$$HO—(CH_2)_n—OH$$

which comprises:
epoxidizing both double bonds of an $\alpha, \omega$-diene of formula (II):

$$CH_2=CH—(CH_2)_{n-4}—CH=CH_2$$

wherein $n \geq 8$ with from 1.8 to 4 moles of hydrogen peroxide, per mole of diolefin starting material, in a double phase, aqueous-organic system in the presence of a catalyst, which is soluble in the organic phase, constituted of a tetraalkylammonium phosphotungstate at a temperature ranging from 40° to 90° C., thereby forming a diepoxide of formula (III):

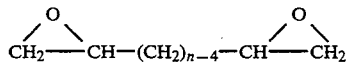

wherein n is as defined above;
(b) separating the diepoxide, which has been prepared, from its reaction medium; and
(c) regioselectively hydrogenating both epoxide groups of diepoxide (III) in a solvent medium at a temperature not greater than 100° C. under a hydrogen pressure ranging from 2 to 5 atm in the presence of a heterogeneous Raney nickel hydrogenation catalyst.

2. The process of claim 1, wherein said Raney nickel catalyst is employed in an amount within the range of from 5 to 40% by weight relative to the weight of diepoxide.

3. The process of claim 2, wherein said Raney nickel catalyst is present in an amount which is within the range of from 10 to 30% by weight of the diepoxide.

4. The process of claim 1, wherein said solvent of the hydrogenation step is selected from the group consisting of ethanol, propanols, butanols, and hydrocarbon solvents.

5. The process of claim 1, wherein the temperature of the hydrogenation reaction ranges from 20° to 100° C.

6. The process of claim 1, wherein the reaction time of the hydrogenation step ranges from 0.5 to 8 hours.

* * * * *